United States Patent [19]

Reger et al.

[11] 4,067,882

[45] Jan. 10, 1978

[54] PROCESS FOR THE PREPARATION OF 2-DIALKOXY PHOSPHINYLIMINO-1,3-DITHIETANE

[75] Inventors: David William Reger, Trenton; Murray Garber; Don Wesley Long, both of Lawrenceville, all of N.J.

[73] Assignee: American Cyanamid Company, Stamford, Conn.

[21] Appl. No.: 695,691

[22] Filed: June 14, 1976

[51] Int. Cl.² ............................................ C07D 339/00
[52] U.S. Cl. ............................................... 260/327 M
[58] Field of Search ..................................... 260/327 M

[56] References Cited

U.S. PATENT DOCUMENTS 3,470,207  9/1969  Addor .................................. 260/327

Primary Examiner—Cecilia M. S. Jaisle
Attorney, Agent, or Firm—Harry H. Kline

[57] ABSTRACT

There is provided a process for preparing 2-diethoxyphosphinylimino-1,3-dithietane by reacting diethoxyphosphinyldithiocarbamate with a methylene halide in an aqueous medium and in the presence of phase transfer catalyst whereby said dithietane is recovered in good yields.

12 Claims, No Drawings

PROCESS FOR THE PREPARATION OF 2-DIALKOXY PHOSPHINYLIMINO-1,3-DITHIETANE

The broad spectrum contact and systemic pesticide 2-diethoxyphosphinylimino-1,3-dithietane represented by the formula (I) below:

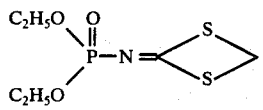

and a method of preparation thereof have been disclosed and claimed in United States Letters Patent No. 3,470,207, issued on Sept. 30, 1969. A method of use thereof has been disclosed and claimed in United States Letters Patent No. 3,553,319 issued on Jan. 5, 1971. The intermediate diethoxyphosphinyldithiocarbamate and a method of preparation thereof have been disclosed and claimed in U.S. Pat. No. 3,476,837 issued on Nov. 4, 1969. Each of the referred to patents is incorporated herein by reference.

It is known that the pesticide of formula (I) is effective for the control of soil dwelling nematodes and, especially, for the control of root-knot nematodes (Meloidognye incognita).

Unfortunately, the preparation of 2-diethoxyphosphinylimino-1,3-dithietane by methods known in the art, while satisfactory for small scale laboratory preparations, is not suitable for large scale preparation of said compound. Thus, it is of considerable interest and importance to be able to prepare 2-diethoxyphosphinylimino-1,3-dithietane on a large scale economically.

In the prior practice, one process consists of three distinct and separate steps as hereinbelow described and graphically illustrated:

Step 1

One molar equivalent of diethoxyphosphoryl chloride is reacted with a 1.1 to 1.2 molar equivalent of ammonium thiocyanate in the presence of an inert solvent, such as benzene, toluene, xylene or the like, at about 20° C to 30° C for a period of time of about 24 hours. The so obtained solution of diethoxyphosphinyl isothiocyanate of formula (III) is washed several times with water and dilute sodium bicarbonate solution, and then the isothiocyanate is isolated by removing the solvent in vacuo. This reaction step may be graphically illustrated as follows:

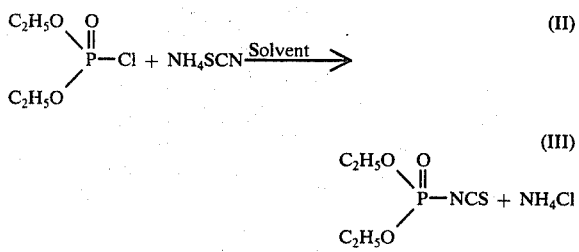

Step 2

The isothiocyanate of formula (III) obtained in Step 1 above, is reacted with a 1.1 to 1.2 molar equivalent of sodium or potassium hydrosulfide, freshly prepared in situ, prior to the addition said isothiocyanate, from hydrogen sulfide and sodium or potassium hydroxide or alkoxide (e.g. t-butoxide) in a lower ($C_1$-$C_3$) alcohol, to yield the corresponding diethoxyphosphinyldithiocarbamate of formula (IV). This reaction is quite rapid and is complete in a relatively short time. The thus obtained dithiocarbamate of formula (IV) may be isolated if desired, but the isolation procedure is cumbersome, and since the dithiocarbamate is relatively unstable it is more convenient to use the "as is" reaction mixture in the following final step. This reaction step may be graphically illustrutated as follows:

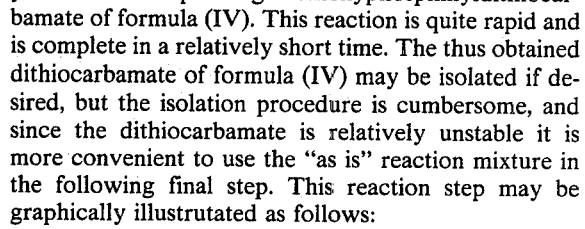

Step 3

To the above reaction mixture, 2.5 to 10 molar equivalents of a methylene halide, selected from methylene bromide, or methylene iodide, are added in the presence of an acid acceptor such as sodium bicarbonate. The reaction mixture is then stirred at room temperature for a period of time from 20 to 24 hours to yield 2-diethoxyphosphinylimino-1,3-dithietane of formula (I). The product dithietane is isolated from the reaction mixture by standard laboratory procedures. The overall reaction can be graphically illustrated as follows:

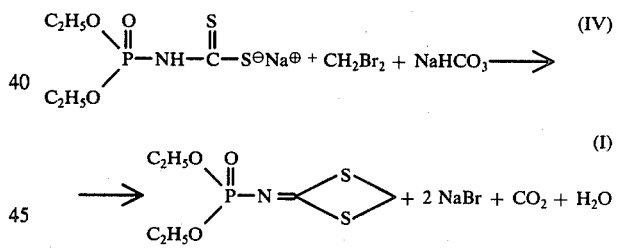

As hereinabove stated, this and similar processes of the art, while suitable for small scale preparation of 2-diethoxyphosphinylimino-1,3-dithietane, are not suitable for large scale manufacturing processes. The required washing of formula (III) intermediate (Step 1) with water and aqueous sodium bicarbonate, to remove impurities, can result in an exothermic decomposition of said intermediate. In addition, the use of solvents, the relatively long reaction times required, and the need for the purification of the intermediates coupled with the inevitable losses suffered during the work-up and purification of the intermediates and of the end product makes this and similar approaches economically undesirable.

It has been unexpectedly found that the 2-diethoxyphosphinylimino-1,3-dithietane of formula (I) can be conveniently prepared on a large scale, in satisfactory yields, from the sodium-, potassium-, or ammonium salt of 2-diethoxyphosphinyldithiocarbamic acid and a methylene halide in water, employing a phase transfer catalyst and controlling the pH of the reaction mixture within well-defined limits, whereby the use of said phase transfer catalyst increases the rate and yield of said reaction and the rigid control of the pH of said reaction minimizes losses, possibly due to the decomposition of the above named intermediates.

The overall process of the present invention involves the following procedure defined and illustrated in detail as follows: A phase transfer catalyst, such as a tri($C_3$-$C_{12}$)-alkylamine, a tri($C_3$-$C_{12}$)alkylmethylammonium salt, a benzyltri($C_2$-$C_3$)alkylammonium salt, a 1,2-dialkyl-3,5-diaryl pyrazolium salt, e.g., 1,2-dimethyl-3,5-diphenylpyrazolium methyl sulfate, a ($C_2$-$C_4$)alkyltriphenylphosphonium salt, alkylpyridinium salts, and the like, is added to an aqueous solution of sodium, potassium or ammonium diethoxyphosphinyldithiocarbamate of formula (IV) in amounts ranging from about 0.1% to 5%, by weight, and, preferably, from 0.5% to 1.5%, by weight, of the solution. Next, a 1.0 to 2.0 molar equivalent of methylene halide such as methylene bromide and methylene iodide, is added to the aqueous solution of the dithiocarbamate of formula (IV). The temperature of the resulting two phase reaction mixture is adjusted to from 25° C to 45° C and, preferably, 28° C to 32° C. The mixture is stirred and an aqueous solution of a base, such as ammonium hydroxide, sodium or potassium hydroxide, sodium or potassium carbonate and sodium or potassium bicarbonate, is added as needed to maintain the pH within a range of 5 to 8 and, preferably, 6 to 7. Under these conditions the reaction is complete in about two to four hours.

Next, the organic phase is separated from the aqueous phase. The latter is extracted with an aromatic solvent such as benzene, toluene and xylene and the aromatic solvent extract is combined with the aforementioned organic phase. The combined mixture is then washed with an aqueous base to obtain a pH of 8. The aqueous extract is then washed with an aromatic solvent and the solvent washings are added to the aforementioned organic phase. There is next recovered the product of formula (I) from the organic phase by removing said aromatic solvent in vacuo.

The above reaction can be graphically illustrated as follows:

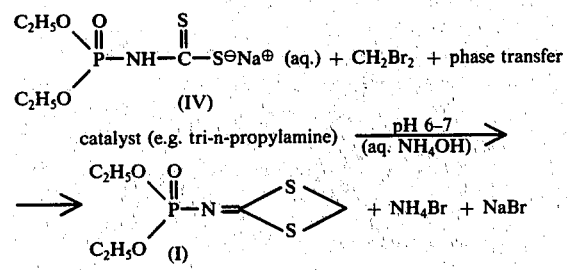

In another embodiment of the present invention it has been found that the above-described procedure can be further modified to good advantage, resulting in improvements in yields and the quality of the product, as follows:

A one to two molar equivalent of a methylene halide, such as methylene bromide and methylene iodide, is admixed with an equal volume of water. A phase transfer catalyst as hereinabove defined is added in the amounts specified above, and the thus-obtained two phase mixture, having a pH of approximately 9, is stirred at a temperature adjusted to 25° C to 45° C.

Next, a 10% to 25%, by volume, aliquot of an aqueous solution of about one molar equivalent of an alkali metal 2-diethoxyphosphinyldithiocarbamate (wherein one molar equivalent of said dithiocarbamate is dissolved in 300 ml to 400 ml of water) is added to the above two phase mixture with stirring. As the reaction commences, the pH of the reaction mixture slowly decreases. When it reaches the range of pH 5 to 8, an aqueous solution of a base is added at a rate to maintain the pH of said reaction in the above specified range. A pH range of 6 to 7 is preferred.

Thereafter, the dithiocarbamate solution is added at a rate so as to coincide with the consumption of the base. Additional amounts of base are added, as needed, to maintain the pH of the reaction mixture in the specified range until the reaction is complete. The reaction time is 2 to 6 hours, and, preferably, from 3 to 5 hours.

On completion of the reaction, the mixture is cooled and the organic phase separated. The aqueous phase is washed with an aromatic solvent such as benzene, toluene and xylene. The organic phase and the aromatic solvent wash are combined, approximately an equal volume of water is added and the pH of the resultant two phase mixture adjusted to 8 and the mixture stirred for about 30 minutes. The organic phase is then separated and the aqueous phase is backwashed with an aromatic solvent, as above. The organic phase and the aromatic solvent wash are combined, and the product of formula (I) is recovered by removing said organic solvent in vacuo until no further weight change of the residue is noted.

Advantageously, the novel procedure of the present invention may be integrated, if so desired, with the reaction steps culminating with the preparation of sodium, potassium or ammonium diethoxyphosphinyldithiocarbamate.

The integrated process, the essential feature of which is the last step comprising the novel procedure of the present invention, is hereinbelow described and illustrated in detail:

One molar equivalent of diethoxyphosphoryl chloride of formula (II) is reacted neat with a 1.0 to 1.2 molar equivalent of anhydrous sodium-, potassium- or ammonium thiocyanate at a temperature range of 5° C to 30° C and, preferably, 15° C to 25° C for a period of time from 2 to 4 hours to yield diethoxyphosphinyl isothiocyanate of formula (III). The reaction is slightly exothermic, but is easily controlled by a cooling bath. The thus-obtained reaction mixture containing the isothiocyanate of formula (III) is used "as is" for the preparation of diethoxyphosphinyldithiocarbamate of formula (IV) as follows:

The above reaction mixture is added slowly to an aqueous solution of a 1.1 to 1.2 molar equivalent of sodium, potassium or ammonium hydrosulfide at a temperature range of 5° C to 30° C and preferably 15° C to 25° C. The ensuing reaction is quite rapid and is complete in about 10 to 15 minutes after the addition of the above reaction mixture is completed. The thus obtained "as is" reaction mixture containing alkali metal diethoxyphosphinyldithiocarbamate is then utilized in the process of the present invention in the following manner: A phase transfer catalyst such as tri-($C_3$-$C_{12}$)alkylmethyl ammonium salts, benzyl-tri($C_2$-$C_3$)alkylammonium salts, 1,2-dialkyl-3,5-diarylpyrazolium salts, such as 1,2-dimethyl-3,5-diphenylpyrazolium methyl sulfate, ($C_2$-$C_4$)alkyltriphenylphosphonium salts, ($C_1$-$C_3$)alkylpyridinium salts and the like, added to the above aqueous reaction mixture in amounts ranging from about 0.1% to 5.0% by weight and preferably 0.5% to 1.5% by weight of the reaction mixture. Next, a 1.0 to 2.0 molar equivalent and preferably a 1.0 to 1.3 molar equivalent of a methylene halide is added to the reaction mixture. The temperature of the resulting two phase reaction mixture is adjusted to about 25° C to 45° C. The mixture is stirred for from 2 to 6 hours, and an aqueous solution of a base is added as needed to maintain a pH range of 5 to 8 and, preferably, 6 to 7. The organic phase is separated and the aqueous phase is extracted with an aromatic solvent such as benzene, toluene and xylene. The latter aromatic solvent extract is combined with the above organic phase. Resultant combined mixture is then washed with an aqueous base and the aqueous extract is washed with an aromatic solvent. The solvent washings are added to the aforementioned organic phase. Finally, the product of formula (I) is recovered from the organic phase by removing the aromatic solvent in vacuo.

The reaction sequence of the overall integrated process hereinabove described can be graphically illustrated as follows:

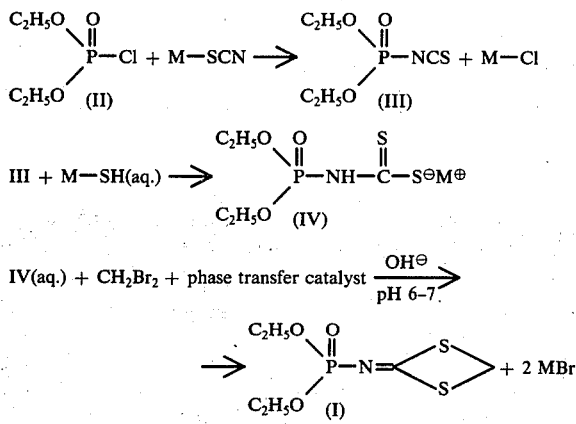

wherein M is an alkali metal, such as sodium or potassium and ammonium.

It is a further advantage of the present invention to introduce an aromatic hydrocarbon solvent such as benzene, toluene and xylene, or an halogenated aliphatic hydrocarbon solvent such as ethylene dichloride, chloroform, methylene chloride and methylene bromide, in Step 1 of the above-described fully integrated process.

The seemingly minor charge in said overall process is quite significant and of great advantage on a large manufacturing scale. First, the above identified thiocyanates are quite hygroscopic and thus tend to absorb moisture from the air while being charged to a reactor containing the diethoxyphosphoryl chloride reactant, and thus normally would require protective blanketing with an inert dry gas, such as nitrogen, and special equipment to load the reactor since the presence of even small amounts of water significantly reduce the overall yields of said process. The use of one of the above-identified solvents in Step 1 allows for the rapid introduction of the thiocyanate into the reactor with minimum exposure to air and the moisture contained therein, and thereafter said solvent serves as a protective liquid blanket preventing said thiocyanate from absorbing moisture from the air and thus eliminates the need for special equipment and an inert gas during the addition of said thiocyanate. Advantageously, this change allows for the addition of diethoxyphosphoryl chloride which is a toxic liquid in a closed system to the stirred slurry of anhydrous thiocyanate in said solvent, and since the ensuing reaction is exothermic, the exotherm is easily controlled by adjusting the rate of said phosphoryl chloride accordingly. Additionally, said solvent serves as an inert diluent and thus allows a more thorough stirring, mixing and pumping of an otherwise thick reaction mixture. Thus, there is no need to employ special, high powered stirring and pumping equipment and, therefore, additional savings in energy requirements can be realized. The presence of said solvent in Step 2 as defined above does not adversely effect the yields of this step. Since solvent is separated from the aqueous phase of the Step 2 reaction mixture when said reaction step is completed, it aids in the removal of solvent soluble impurities which may be present in said mixture.

Further, it has been found convenient to substitute the Step 3 methylene halide reactant for the solvent in Step 1 of the above integrated process, wherein it will serve as an inert solvent-diluent. Under these conditions, the methylene halide is also present in Step 2. However, in Step 3, it becomes a reactant. This modification does not significantly influence the overall yields obtainable by said process.

In the overall preferred integrated process, the essential feature resides in the last step and is hereinbelow described as follows:

To a stirred slurry of 1.0 to 1.2 molar equivalent of anhydrous sodium-, potassium- or ammonium thiocyanate in about 50 ml to 100 ml of a solvent, such as benzene, toluene, xylene, ethylene dichloride, chloroform, methylene chloride and methylene bromide, one molar equivalent of diethoxyphosphoryl chloride of formula (II) is added at a temperature range of 5° to 30° C and, preferably, from 15° to 25° C, while stirring for a period of time from 2 to 4 hours to yield diethoxyphosphinyl isothiocyanate of formula (III). The reaction is slightly exothermic, and controlled by either adjusting the rate of addition of said phosphoryl chloride or employing a cooling bath or even using both.

The above reaction mixture containing the diethoxyphosphinyl isothiocyanate, is then added slowly to an aqueous solution of 1.1 to 1.2 molar equivalent of sodium-, potassium- or ammonium hydrosulfide at a temperature range of 5° to 35° C and, preferably, 25° to 30° C. The ensuing reaction is quite rapid and is complete in about 10 to 15 minutes after the addition of the reaction mixture is completed. Next, the organic phase of the thus obtained two phase reaction mixture is separated from the aqueous phase, and is discarded or recovered for reuse. The aqueous phase, containing the diethoxyphosphinyldithiocarbamate, is utilized in the novel procedure of the present invention as follows:

A phase transfer catalyst as hereinabove described is added in the amounts specified, to a mixture of a 1.0 to 2.0 molar equivalent and, preferably, a 1.0 to 1.3 molar equivalent of methylene bromide (or iodide) and an equal volume of water. The temperature of the stirred two phase mixture is adjusted to about 25° to 45° C and preferably 28° to 32° C. Immediately thereafter, 10% to 25%, by volume, of the aqueous solution of the dithiocarbamate of formula (IV) obtained in the above reaction step is added to said mixture. As the reaction commences, the pH of the reaction mixture slowly decreases and when it reaches the range of pH 5 to 8, and preferably 6 to 7, an aqueous solution of a base is added at a rate to maintain the pH of said reaction in the above specified range.

Thereafter, the remaining dithiocarbamate solution is added at a controlled rate so as to maintain a steady consumption of base with cooling as needed to keep the temperature in the range of 25° to 40° C. Additional amounts of base are added, as needed, to maintain the pH of the reaction in the specified range until the reaction is complete. The reaction time is 2 to 6 hours and preferably 4 to 5 hours.

On completion of the reaction, the mixture is cooled and the organic phase is separated. The aqueous phase is washed with a suitable organic solvent. The organic phase and the solvent wash are combined. Approximately, an equal volume of water is added. The pH of the resultant two phase mixture is adjusted to 8 and the mixture stirred for about 30 minutes. The organic phase is then separated. The aqueous phase is next washed with a solvent as above. The washings are combined with the organic phase. The product of formula (I) is recovered by removing said organic solvent in vacuo. In the thus described integrated process, culminating with the novel procedure of the present invention, overall yields of 60% to 79% of theory are realized.

Advantageously, analogs of formula (I) 2-diethoxyphosphinylimino-1,3-dithietane represented by formula:

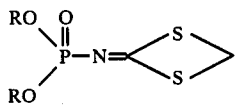

wherein R is an alkyl radical, such as methyl, ethyl, n-propyl, isopropyl or t-butyl can be prepared by the novel process of the present invention.

Resultant 2-diethoxyphosphinylimino-1,3-dithietanes can be formulated for use as nematocides by accepted methods as liquid or emulsifiable concentrates, wettable powders, dusts, dust concentrates and granular formulations.

The following non-limiting examples are incorporated therein to further illustrate the present invention.

EXAMPLE 1

Preparation of 2-diethoxyphosphinylimino-1,3-dithietane using a phase transfer catalyst To a suitable reactor vessel containing diethoxyphosphoryl chloride (130 g.; 0.8 mole) is added dry ammonium thiocyanate (67.0 g; 0.88 mole) over a 10 minute period at 5° C with stirring. Resultant reaction is exothermic and the temperature of the reaction mixture is maintained below 25° C with an ice bath. A slurry is formed which is allowed to warm to 25° C and stirred for 4 hours. It is next cooled to 5° C and washed for 3 minutes with cold water (170 ml). The aqueous phase separated and discarded.

Diethoxyphosphinyl isothiocyanate so obtained is immediately used by slowly adding it to a solution of sodium hydrosulfide monohydrate (74.0 g - 73% real; 1.0 mole) in water (200 ml) at 5° C. Resultant reaction is also exothermic and the temperature of the reaction is maintained below 25° C by controlling the rate of addition of the isothiocyanate. The formed slurry of sodium diethoxphosphinyldithiocarbamate is stirred an additional 10 minutes at 15° to 20° C after the addition of the isothiocyanate is completed.

Benzyltriethylammonium chloride (3.0 g) is added to the dithiocarbamate slurry and the pH of the system adjusted from 7.7 to 6.0 with concentrated hydrochloric acid (8.5 ml). Methylene bromide (139.1 g; 0.80 mole) is then added to the slurry. The reaction mixture is stirred at 25° to 27° C and ammonium hydroxide solution (15%) added as needed to maintain the pH at 6.0. The reaction is run for 18½ hours and a total of 106 ml of 15% ammonium hydroxide is added.

The organic phase is separated, the aqueous phase washed with toluene (2 × 50 ml) and the toluene washings are combined with the organic phase. The combined organic phase is washed with saturated aqueous sodium bicarbonate solution (3 × 100 ml). The combined sodium bicarbonate solutions are backwashed with toluene (50 ml) and the toluene layer added to the above organic phase. The organic phase is evaporated to constant weight to afford 148.6 g (85.6% real; 66.1% yield) of 2-diethoxyphosphinylimino-1,3-dithietane.

EXAMPLE 2

Repeating the procedure of Example 1 in every detail except that methylene iodide is substituted for methylene bromide, 2-diethoxyphosphinylimino-1,3-dithietane is obtained in substantially the same yields.

EXAMPLE 3

Preparation of 2-diethoxyphosphinylimino-1,3-dithietane using various phase transfer catalysts The procedure of Example 1 is repeated in every respect except that the benzyltriethylammonium chloride is replaced with:

1. tri-n-propylamine, and the reaction terminated after 5 hours, to afford 150 g (86.7% real; 67.4% yield) of title product; or
2. tri-n-butylamine, and the reaction is terminated after 3 hours and 54 minutes, to afford 140.1 g (87.3% real; 63.4% yield) of title product; or
3. tricaprylmethylammonium chloride, and the reaction is terminated in 3½ hours, to afford 144.1 g (85.8% real; 64.1% yield) of title product; or
4. triisodecylamine, and the reaction is terminated after 5¾ hours, to afford 150 g (86.6% real; 67.3% yield) of title product; or
5. 1,2-Dimethyl-3,5-diphenylpyrazolium methyl sulfate, and the reaction is terminated in 4 hours and 26 minutes to afford 146.7 g (87.9% real; 66.8% yield) of title product; or
6. Isopropyltriphenylphosphonium iodide; and the reaction is terminated in 1 hour and 55 minutes to afford 136.1 g (82.1% real; 57.9% yield) of title product; or
7. Methylpyridinium iodide, and the reaction is terminated in 3 hours and 15 minutes to afford 131.9 g (81.9% real; 55.9% yield) of title product.

EXAMPLE 4

Preparation of 2-diethoxyphosphinylimino-1,3-dithietane by an integrated three step process using tri-n-propylamine as phase transfer catalyst Dry ammonium thiocyanate (67.0 g; 0.88 mole) is added at 5° C over 10 minutes to diethoxyphosphoryl chloride (138.0 g; 0.80 mole) with stirring. The ensuing reaction is exothermic, and an ice bath is used to maintain the reaction temperature below 25° C. The resulting slurry of diethoxyphosphinyl isothiocyanate is allowed to warm to 25° C and is then stirred for 3 hours.

The slurry is then cooled to 5° C and added slowly to a solution of sodium hydrosulfide monohydrate (74.0 g; 73% real; 1.0 mole) in water (175 ml) at 5° C. The ensuing reaction is also exothermic and the temperature of the reaction mixture is held below 25° C by appropriately adjusting the rate of addition of the isothiocyanate slurry. The slurry of sodium diethoxyphosphinyldithiocarbamate formed in the reaction is stirred an additional 10 minutes at 15° to 25° C after the addition of the isothiocyanate is completed.

Tri-n-propylamine (3.0 g) is added to the above dithiocarbamate slurry, and the pH of the reaction mixture is then adjusted from 7.7 to 6.4 with concentrated hydrochloric acid (6 ml). Next, methylene bromide (139.0 g; 0.80 mole) is added to the slurry, the mixture is stirred at 30° C and 15% aqueous ammonium hydroxide added as needed to maintain the pH at 6.0. The reaction is run for 3 hours and 39 minutes and during this time a total of 117 ml of 15% aqueous ammonium hydroxide is added.

The organic phase is separated, the aqueous phase is washed with toluene (50 ml) and the toluene wash combined with the organic phase. The combined organic phase is washed with saturated aqueous sodium bicarbonate solution (3 × 100 ml). The combined sodium bicarbonate solutions are backwashed with toluene (50 ml) and the toluene wash combined with the organic phase. The organic phase is then stripped to constant weight to afford 148.0 g (82.6% real; 63.3% yield) of 2-diethoxyphosphinylimino-1,3-dithietane.

EXAMPLE 5

Preparation of
2-diethoxyphosphinylimino-1,3-dithietane by a fully
integrated 3-step process using tri-n-propylamine as
phase transfer catalyst and methylene bromide as
solvent-reactant To a stirred slurry of dry sodium thiocyanate (71.3 g; 0.88 mole) in methylene bromide (139.1 g; 0.80 mole) at 10° C diethoxyphosphoryl chloride (138.0 g; 0.80 mole) is added. The reaction mixture is allowed to warm up to 25° C, and is stirred at 25° C for 3 hours.

The resulting slurry of diethoxyphosphinyl isothiocyanate is then added slowly over 1 hour to a solution of sodium hydrosulfide monohydrate (74.0 g – 73% real; 1.0 mole) in water (200 ml). The ensuing reaction is exothermic and the temperature of the reaction mixture is maintained between 10° and 25° C with an ice bath. After the addition of the slurry is completed, tri-n-propylamine (3.0 g) is added and the temperature of the reaction mixture adjusted to 30° C. Stirring is continued at 30° C until the pH of the reaction mixture drops from 9.5 to 6.5 in about 10 minutes. Thereafter 28% aqueous ammonium hydroxide solution is added as needed to maintain the pH at 6.5. Over a 2 hour and 15 minute reaction time a total of 48 ml of ammonium hydroxide solution is added.

The reaction temperature is then adjusted to 15° C and toluene (200 ml) added to the reaction mixture. The resulting two phase mixture is separated, and the organic phase recycled to the reaction vessel. The aqueous phase is washed with toluene (50 ml) and the toluene washings are kept.

The organic phase is stirred for 10 minutes at 25° C with saturated aqueous sodium bicarbonate solution (100 ml), the two phase mixture is separated and the organic phase recycled to the reaction vessel. A second portion of saturated aqueous sodium bicarbonate solution (300 ml) is added and the mixture stirred 1 hour at 25° C and then the organic phase is again separated.

The above sodium bicarbonate wash liquors are combined in a separatory funnel with sodium chloride (78 g) and with the above toluene (50 ml) wash. The resulting mixture is shaken vigorously for 10 minutes and is then filtered. The toluene phase is separated and combined with the above isolated organic phase.

The thus obtained mixture is stripped to constant weight to afford 142.0 g (83.2% real; 61.2% yield) of 2-diethoxyphosphinylimino-1,3-dithietane.

EXAMPLE 6

Preparation of
2-Diethoxyphosphinylimino-1,3-dithietane by a fully
integrated process To stirred slurry of dry sodium thiocyanate (892 g; 11 mole) in toluene (600 ml) at 20° C diethoxyphosphoryl chloride (1725 g; 10 mole) is added. After the addition is completed the reaction mixture is stirred at 25° C for 3 hours.

The diethoxyphosphinyl isothiocyanate obtained above is added over 1 hour to a solution of sodium hydrosulfide monohydrate (925 g; 12.5 mole) in water (3750 ml). The ensuing reaction is exothermic. The temperature of the reaction mixture is maintained between 20° and 30° C. After the addition is completed, the temperature is adjusted to 30° C, the two phase mixture is separated and the toluene phase discarded.

Water (905 ml), methylene bromide (2265 g; 13.0 mole) and tri-n-propylamine (12.5 g) are charged into a reaction vessel. The pH of the two phase mixture is 9.1. The temperature of the mixture is adjusted to 30° C and 13% of the aqueous dithiocarbamate solution obtained in the above step is added to the mixture. The pH of the reaction mixture drops to 6.5 during a 1 hour period. Concentrated ammonium hydroxide is added to maintain the pH between 6 and 7. The reaction is run by periodically adding 15% to 20% of the aqueous dithiocarbamate solution to the reaction mixture, followed by the addition of concentrated ammonium hydroxide to maintain the pH between 6 and 7. The reaction time is 5 hours and 17 minutes and a total of 635 ml of ammonium hydroxide is used.

The reaction mixture is then cooled to 25° C and the organic phase separated. The aqueous phase is backwashed with toluene (2500 ml) and then discarded. The above organic phase and the toluene wash are recycled to the reaction vessel. Water (3125 ml) is added, the pH of the two phase system adjusted to 8 with ammonium hydroxide solution, and the mixture is stirred for 30 minutes. The organic phase is then separated and stripped to constant weight in vacuo to afford 1853 g (89.0% real; 68.3% yield) of title product.

The aqueous layer of the final wash is backwashed with toluene (2000 ml) for 15 minutes. The toluene phase is separated and stripped to constant weight in vacuo to afford 72.4 g (93.6% real; 2.8% yield) of title product.

Total yield of product obtained is 71.1%.

Substitution of dimethoxyphosphoryl chloride, dipropoxyphosphoryl chloride, diisopropoxyphosphoryl chloride and di-n-butoxyphosphoryl chloride for diethoxyphosphoryl chloride in the above process affords 2-dimethoxyphosphinylimino-1,3-dithietane, 2-dipropoxyphosphinylimino-1,3-dithietane, 2-diisopropoxyphosphinylimino-1,3-dithietane and 2-di-n-butoxyphosphinylimino-1,3-dithietane, respectively.

EXAMPLE 7

Preparation of 2-Diethoxyphosphinylimino-1,3-dithietane by a fully integrated 3-step process using tri-n-propylamine as phase transfer catalyst and methylene bromide as solvent-reactant To a stirred slurry of dry sodium thiocyanate (71.3 g; 0.88 mole) in methylene bromide (139.1 g; 0.80 mole) at 10° C diethoxyphosphoryl chloride (138.0 g; 0.80 mole) is added. The resulting reaction mixture is allowed to warm up to 25° C, and is stirred at 25° C for 3 hours.

The resulting slurry of diethoxyphosphinyl isothiocyanate obtained above is then added slowly over 1 hour to a solution of sodium hydrosulfide monohydrate (74.0 g – 73% real; 1.0 mole) in water (200 ml). The ensuing reaction is exothermic and the temperature of the reaction mixture is maintained between 10° and 25° C with an ice bath. After the addition of the slurry is completed tri-n-propylamine (3.0 g) is added and the temperature of the reaction mixture adjusted to 30° C. Stirring is continued at 30° C until the pH of the reaction mixture drops from 9.5 to 6.5. Thereafter 28% ammonium hydroxide solution is added as needed to maintain a pH of 6.5. Over a 2 hour and 15 minute reaction time a total of 51 ml of ammonium hydroxide solution is added.

The reaction temperature is then adjusted to 15° C and toluene (50 ml) added to the reaction mixture. The resulting two phase mixture is separated, and the organic phase recycled to the reaction vessel. The aqueous phase is washed with toluene (150 ml) and the toluene washings are also recycled to the reaction vessel. Next, water (300 ml) is added to the reaction vessel and the resulting two phase system stirred at 25° C for 1 hour. The organic phase is separated, the aqueous phase is recycled to the reaction vessel, toluene (200 ml) added, and the resulting two phase system is stirred for 10 minutes. The organic phase is separated and the thus obtained two organic phases are separately stripped to dryness in vacuo to afford 135 g (85.7% pure) product from the main fraction and 12.2 g (86.9% pure) product from the second fraction.

Total yield: 126.3 g real (65.4% yield) of title product.

EXAMPLES 8-10

Preparation of 2-Diethoxyphosphinylimino-1,3-dithietane by an integrated process to study the effect of a phase transfer catalyst on the rate of the reaction Anhydrous ammonium thiocyanate (67.0 g; 0.88 mole) is added over a 10 minute period at 5° C with stirring to diethoxyphosphoryl chloride (138.0 g; 0.80 mole). The ensuing reaction is exothermic and the temperature of the reaction mixture is maintained below 25° C with an ice bath. The resulting slurry is allowed to warm to 25° C and stirred for 4 hours.

The above reaction mixture, containing the diethoxyphosphinyl isothiocyanate and all the impurities and/or by products formed in the reaction, is added slowly to a solution of sodium hydrosulfide monohydrate (74.0 g -73% real; 1.0 mole) in water (200 ml) at 5° C. The ensuing reaction is also exothermic and the temperature of the reaction is maintained below 25° C by controlling the rate of addition of the isothiocyanate. The resulting slurry of sodium diethoxyphosphinyldithiocarbamate is stirred an additional 10 minutes at 15° C to 20° C after the addition of the isothiocyanate is completed.

Tri-n-propylamine (3.0 g) and methylene bromide (139.1 g; 0.80 mole) are then added to the slurry. The reaction mixture is stirred at 30° C and ammonium hydroxide solution (15%) added as needed to maintain the pH at 6.0. The theoretical amount of ammonium hydroxide (94 ml) needed to maintain the above pH is taken up in 2 hours and 3 minutes. The reaction is run an additional 1 hour and 36 minutes at pH 6 requiring the addition of ammonium hydroxide (20 ml) to maintain the above pH.

The organic phase is separated, the aqueous phase washed with toluene (2×50 ml) and the toluene washings are combined with the organic phase. The combined organic phase is washed with saturated aqueous sodium bicarbonate solution (3×100 ml). The combined sodium bicarbonate solutions are backwashed with toluene (50 ml) and the toluene layer added to the above organic phase. The organic phase is evaporated in vacuo to constant weight to afford 148.0 g (82.6% real; 63.3% yield) of 2-diethoxyphosphinylimino-1,3-dithietane.

The above procedure is repeated, except no tri-n-propylamine is added in step 3. The theoretical amount of ammonium hydroxide needed to maintain pH 6 is taken up in 7 hours and 29 minutes, the reaction is run an additional hour, requiring additional ammonium hydroxide to maintain pH 6. There is obtained 124.7 g (89.3% real; 57.7% yield) of 2-diethoxyphosphinylimino-1,3-dithietane.

The above procedure is repeated, except that instead of water, 200 ml of aqueous acetone (10% by volume acetone) is used in steps 2 and 3 and no tri-n-propylamine phase transfer catalyst is used. The theoretical amount of ammonium hydroxide needed to maintain pH 6-7 is taken up in 5 hours and 3 minutes. The reaction is run an additional 3 hours and 29 minutes, requiring additional ammonium hydroxide to maintain the above pH.

There is obtained 146.0 g (79.1% real; 59.8% yield) of 2-diethoxyphosphinylimino-1,3-dithietane.

EXAMPLE 11

Evaluation of 2-diethoxyphosphinylimino-1,3-dithietane for the control of root-knot nematode (Meloidogyne incognita) on tomato in the greenhouse.

A. Material

2-Diethoxyphosphinylimino-1,3-dithietane.

B. Plant

Tomato (Lycopersicon esculentum; Cv. Bonny Best).

C. Infective Agent

Root-knot nematode (Meloidogyne incognita) inoculum.

Application Rates/Liter of Potting Soil
Equivalent to Pound/Acre - Broadcast

2-Diethoxyphosphinylimino-1,3-dithietane at 0.75 mg, 1.5 mg and 3.0 mg/liter of soil.

Procedure

Acetone solutions of the sample are prepared at the appropriate concentrations.

One liter of moist potting soil is placed in a suitable stainless steel beaker. One ml of candidate solution is distributed, drop by drop, over the surface of the soil. The beaker is then capped and placed on an off-center rotary mixer and mixed for 2 minutes (about 60 revolutions). After mixing, the soil is divided between two 0.5 liter paper cups by filling the cups half full of soil then distributing 25 ml root-knot nematode inoculum on the soil and filling the remainder of the container with treated soil. Seedling tomato plants are transplanted into the cups of soil the same day, watered and removed to the greenhouse. After about 4 weeks, the tomato plants are carefully removed from the containers, the soil washed away from the roots, and the roots are then examined for nematode galling.

The roots are indexed for galling by the following system:

O = No visible galling
T = Less than 1% of root galls.
1 = 1–5% of roots galled.
2 = 6–10% of roots galled.
3 = 11–20% of roots galled.
4 = 21–30% of roots galled.
5 = 31–40% of roots galled.
6 = 41–50% of roots galled.
7 = 51–60% of roots galled.
8 = 61–70% of roots galled.
9 = 71–80% of roots galled.
10 = 81–100% of roots galled.

The results obtained are summarized in Table I.

Table I

Evaluation of 2-Diethoxyphosphinylimino-1,3-dithietane for the Control of Root-knot Nematode (Meloidogyne incognita) on Tomato in the Greenhouse

| Compound | Rate mg/l | Root-knot Index 1 | 2 | 3 | Average of 3 Replicates |
|---|---|---|---|---|---|
| 2-Diethoxyphosphinylimino-1,3-dithietane | 0.75 | 8 | 8 | 5 | 7.0 |
|  | 1.5 | 6 | 6 | 2 | 4.7 |
|  | 3.0 | 0 | 0 | T | 0–T |
| Infected Controls | — | 10 | 10 | 10 | 10.0 |
| Non-infected Controls | — | 0 | 0 | 0 | 0.0 |

We claim:

1. The process for the preparation of a dithietane having the formula:

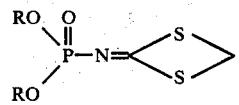

wherein R is a $C_1$-$C_4$ alkyl radical comprising: reacting one molar equivalent of a compound of formula:

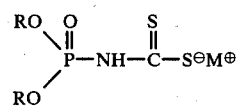

wherein R is as defined above; M is a cation selected from the group consisting of sodium, potassium and ammonium in the presence of water, with a one to two molar equivalent of a methylene halide selected from the group consisting of methylene bromide and methylene iodide in the presence of 0.1% to 5%, by weight, of the reaction mixture of a phase transfer catalyst selected from the group consisting of a tri-($C_3$-$C_{12}$)alkylamine, a tri-($C_3$-$C_{12}$)alkylmethylammonium salt, a benzyltri-($C_2$-$C_3$)alkylammonium salt, a 1,2-dialkyl-3,5-diarylpyrazolium salt, a $C_2$-$C_4$ alkyltriphenylphosphonium salt and a $C_1$-$C_3$ alkylpyridinium salt at a temperature ranging from 25° C to 45° C and a pH of 5 to 8 for a period of time sufficient to essentially complete the reaction, and recovering said dithietane compound.

2. The process according to claim 1, wherein the amount of phase transfer catalyst is 0.5% to 1.5%, by weight, of the reaction mixture; the temperature range is 28° C to 32° C; and the pH range is 6 to 7.

3. The process according to claim 1, wherein R is ethyl; M is sodium; the methylene halide is methylene bromide; the phase transfer catalyst is selected from the group consisting of tri-n-propylamine, tri-n-butylamine, triisodecylamine, tricaprylmethylammonium chloride, benzyltriethylammonium chloride, methylpyridinium iodide, 1,2-dimethyl-3,5-diphenylpyrazolium methyl sulfate and isopropyltriphenylphosphorium iodide in an amount ranging from 0.5% to 1.5%, by weight of the reaction mixture; the temperature of the reaction is 28° C to 32° C; and the pH range is 6 to 7.

4. The process according to claim 3, wherein the phase transfer catalyst is tri-n-propylamine.

5. The process for the preparation of a compound according to claim 1 represented by the formula:

$$\begin{array}{c}RO\diagdown\overset{O}{\underset{\displaystyle\parallel}{}}\\ \diagup P-N=\hspace{-4pt}\begin{array}{c}S\diagdown\\ \diagup\\ S\diagup\end{array}\\ RO\end{array}$$

wherein R is a $C_1$-$C_4$ alkyl radical comprising: reacting one molar equivalent of a compound of formula:

$$\begin{array}{c}RO\diagdown\overset{O}{\underset{\displaystyle\parallel}{}}\\ \diagup P-Cl\\ RO\end{array}$$

wherein R is as defined above with a 1.0 to 1.2 molar equivalent of an anhydrous thiocyanate selected from sodium-, potassium and ammonium thiocyanate at a temperature range of 5° C to 30° C for a period of time sufficient to essentially complete the reaction to obtain a compound of formula:

$$\begin{array}{c}RO\diagdown\overset{O}{\underset{\displaystyle\parallel}{}}\\ \diagup P-NCS\\ RO\end{array}$$

wherein R is as defined above, reacting the thus—latter formed compound without isolation from the above reaction mixture, in the presence of water with 1.1 to 1.2 molar equivalent of sodium hydrosulfide, potassium hydrosulfide or ammonium hydrosulfide, at a temperature range of 5° C to 30° C for a period of time sufficient to essentially complete the reaction to obtain a compound of formula:

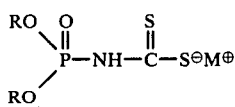

wherein R is as defined above; and M is a cation selected from the group consisting of sodium, potassium and ammonium, reacting the thus—latter formed compound without isolation from the above reaction mixture with a one to 2.0 molar equivalent of a methylene halide selected from the group consisting of methylene bromide and methylene iodide in the presence of 0.1% to 5%, by weight, of the reaction mixture of a phase transfer catalyst selected from group consisting of a tri-(C$_3$-C$_{12}$)-alkylamine, a tri-(C$_3$-C$_{12}$)alkylmethylammonium salt, 1,2-dialkyl-3,5-diarylpyrazolium salt, a benzyl-tri-(C$_2$-C$_3$)alkylammonium salt, a C$_2$-C$_4$ alkyltriphenylphosphonium salt and a C$_1$-C$_3$ alkylpyridinium salt at a temperature range of 25° C to 45° C and a pH range of 5 to 8, for a period of time sufficient to essentially complete the reaction, and recovering resultant dithietane in good yield and purity.

6. A process according to claim 5, wherein the thiocyanate is sodium thiocyanate and the pH range is 6 to 7.

7. The process for the preparation of a compound according to claim 1 represented by the formula:

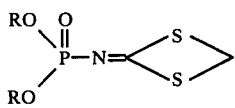

wherein R is C$_1$-C$_4$ alkyl comprising: bringing into reactive combination a one molar equivalent of a compound having the formula:

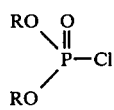

wherein R is as defined above to a slurry of 1 to 1.2 molar equivalent of an anhydrous thiocyanate selected from the group consisting of sodium-, potassium-, and ammonium thiocyanate in an anhydrous organic solvent selected from the group consisting of benzene, toluene, xylene, ethylene dichloride, chloroform, methylene chloride and methylene bromide, agitating said mixture at a temperature ranging from 5° C to 30° C to form a mixture comprising the reaction and obtain a compound of formula:

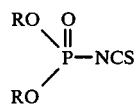

wherein R is as defined above, adding the latter reaction mixture containing said compound to an aqueous solution of a 1.1 to 1.2 molar equivalent of a hydrosulfide selected from the group consisting of sodium-, potassium-, and ammonium hydrosulfide, agitating said two phase mixture at a temperature ranging from 5° C to 30° C to obtain a compound of formula:

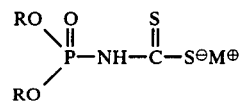

wherein R is as defined above, and M is sodium potassium or ammonium, separating resultant aqueous phase containing the above dithiocarbamate compound from an organic phase, adding said aqueous phase to a mixture of a one to 1.3 molar equivalent of a methylene halide and an equal volume of water containing a phase transfer catalyst selected from the group consisting of a tri-(C$_3$-C$_{12}$)alkylamine, a tri-(C$_3$-C$_{12}$)alkylmethylammonium salt, a 1,2-dialkyl-3,5-diarylpyrazolium salt, a benzyl- tri-(C$_2$-C$_3$)alkylammonium salt, a C$_2$-C$_4$ alkyltriphenylphosphonium salt, a C$_1$-C$_3$ alkylpyridinium salt, said catalyst being present in an amount ranging from 0.1% to 5%, by weight, of the reaction mixture, adding an aqueous solution of a base selected from the group consisting of sodium-, potassium- and ammonium hydroxide, sodium and potassium carbonate and bicarbonate at a rate, sufficient to maintain the pH of the reaction mixture in the range of 5 to 8 while simultaneously controlling the rate of addition of said aqueous solution of said dithiocarbamate and said base, and recovering resultant dithietane in good yield.

8. The process according to claim 7, wherein the thiocyanate is sodium thiocyanate, the hydrosulfide is sodium hydrosulfide and the pH range is 6 to 7.

9. The process according to claim 7, wherein R is ethyl, the thiocyanate is sodium thiocyanate, the aromatic solvent is toluene, the hydrosulfide is sodium hydrosulfide, the methylene halide is methylene bromide, and the phase phase transfer catalyst is tri-n-propylamine.

10. The process for the preparation of a compound according to claim 1 having the formula:

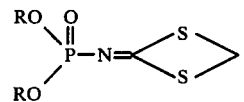

wherein R is C$_1$-C$_4$ alkyl, comprising: adding a one molar equivalent of a compound of formula:

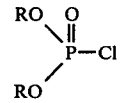

wherein R is as defined above, to a slurry of 1.1 molar equivalent of an anhydrous thiocyanate selected from sodium-, potassium-, and ammonium thiocyanate in a one to 2.0 molar equivalent of a methylene halide selected from methylene bromide and methylene iodide; reacting said mixture at a temperature range of 5° C to 30° C to obtain a compound of formula:

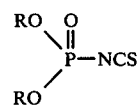

wherein R is as defined above, adding the above reaction mixture containing said latter compound to an aqueous solution of a 1.1 to 1.2 molar equivalent of a hydrosulfide; selected from the group consisting of sodium-, potassium-, and ammonium hydrosulfide, reacting the latter resulting two phase mixture at a temperature range of from 5° C to 30° C to obtain methylene halide and a compound of formula:

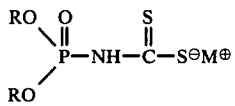

wherein R is as defined above, and M is sodium, potassium or ammonium, adding a phase transfer catalyst selected from the group consisting of a tri-$(C_3-C_{12})$alkylamine, a tri-$(C_3-C_{12})$alkylmethylammonium salt, a 1,2-dialkyl-3,5-diarylpyrazolium salt, a benzyl-tri-$(C_2-C_3)$alkylammonium salt, a $C_2-C_4$ alkyltriphenylphosphonium salt, a $C_1-C_3$ alkylpyridinium salt in an amount ranging from 0.1% to 5%, by weight, of the reacting said latter mixture at a temperature range of 25° C to 45° C, and adding thereto an aqueous solution of a base selected from the group consisting of sodium hydroxide, potassium hydroxide, ammonium hydroxide, sodium carbonate, potassium carbonate and the corresponding bicarbonate to maintain the pH of the reaction mixture in the range of 5 to 8; and recovering resultant dithietane in good yield.

11. The process according to claim 10, wherein the methylene halide is methylene bromide, the thiocyanate is sodium thiocyanate, the hydrosulfide is sodium hydrosulfide, and the pH range 6 to 7.

12. The process according to claim 10, wherein R is ethyl, the methylene halide is methylene bromide, the thiocyanate is sodium thiocyanate, the hydrosulfide is sodium hydrosulfide, the phase transfer catalyst is tri-n-propylamine, the base is ammonium hydroxide, and the pH range is 6 to 7.

* * * * *